(12) United States Patent
Minnich et al.

(10) Patent No.: US 6,365,368 B1
(45) Date of Patent: Apr. 2, 2002

(54) RAPID METHOD FOR THE DETECTION AND QUANTIFICATION OF MICROBES IN WATER

(75) Inventors: Scott A. Minnich, Princeton, NJ (US); Steven A. Lobel, Augusta, GA (US); Gerald Schochetman, Rockville, MD (US); Peter Feng, Rockville, MD (US); Richard Massey, Rockville, MD (US)

(73) Assignee: IGEN International, Inc., Gaithersburg, MD (US)

( * ) Notice: Subject to any disclaimer, the term of this patent is extended or adjusted under 35 U.S.C. 154(b) by 0 days.

(21) Appl. No.: 07/987,233

(22) Filed: Dec. 7, 1992

Related U.S. Application Data

(63) Continuation of application No. 07/388,957, filed on Aug. 2, 1989, now abandoned, which is a continuation of application No. 06/733,219, filed on May 10, 1985, now abandoned.

(51) Int. Cl.[7] ............................................. G01N 33/543
(52) U.S. Cl. ........................ 435/34; 435/7.1; 435/7.2; 435/7.3; 435/7.37; 435/7.92; 435/29; 435/33; 435/38; 435/40; 435/848; 435/849; 435/287.1; 436/177; 436/178; 436/809
(58) Field of Search ..................... 435/7.1, 7.2, 7.3, 435/7.37, 7.92, 29, 33, 34, 38, 40, 6, 848, 849, 287.1, 293, 300; 436/177, 178, 809

(56) References Cited

U.S. PATENT DOCUMENTS

| | | | | |
|---|---|---|---|---|
| 4,443,549 A | * | 4/1984 | Sadowski | 436/548 |
| 4,493,815 A | * | 1/1985 | Fernwood et al. | 422/101 |
| 4,592,994 A | * | 6/1986 | Mattiason | |
| 4,652,533 A | * | 3/1987 | Jolley | 436/518 |
| 4,704,255 A | * | 11/1987 | Jolley | 422/101 |

OTHER PUBLICATIONS

Singer, R.H., et al., *Biotechniques*, vol. 4, No. 3, pp. 230–243, 1986.*

Feng, P.C.S., et al, App. Environ. Microbiol., vol. 43, No. 6, Jun. 1982, pp. 1320–1329.*

* cited by examiner

*Primary Examiner*—Christopher L. Chin
(74) *Attorney, Agent, or Firm*—Kramer Levin Naftalis & Frankel LLP; Barry Evans, Esq.

(57) ABSTRACT

The present invention concerns methods of testing water for microbe contamination. The methods of the invention comprise supplementing existing methods with assays using specific reagents such as monoclonal antibodies. The invention also concerns a device for use in the methods of the invention.

21 Claims, 1 Drawing Sheet

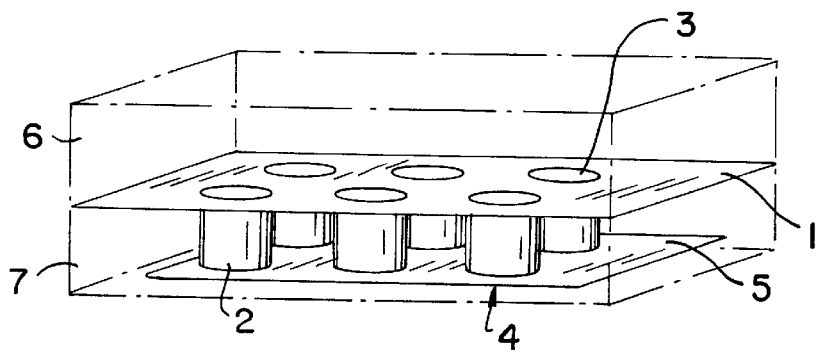
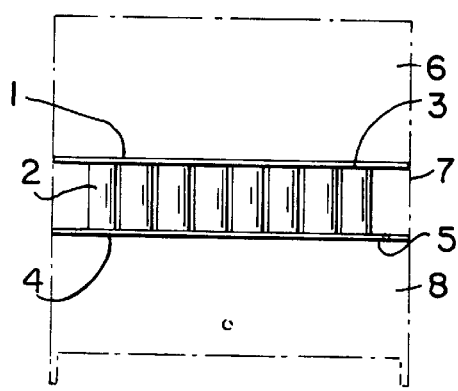
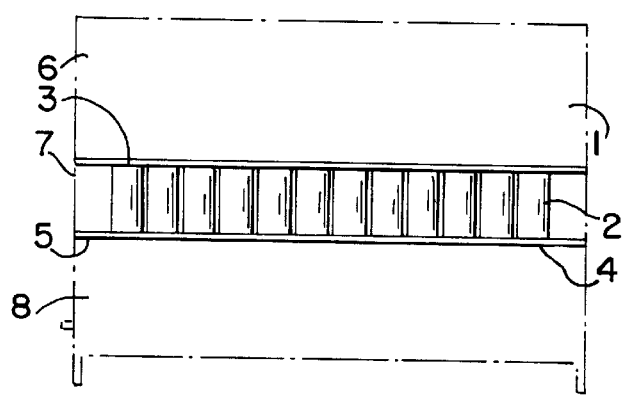
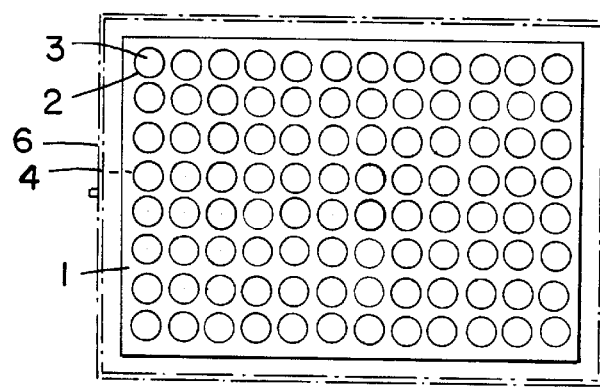

RAPID METHOD FOR THE DETECTION AND QUANTIFICATION OF MICROBES IN WATER

This application is a continuation of application Ser. No. 07/388,957, filed Aug. 2, 1989, now abandoned, which in turn is continuation of application Ser. No. 06/733,219, filed May 10, 1985, now abandoned.

BACKGROUND OF THE INVENTION

Detection and enumeration of indicator bacteria is of primary importance for monitoring the sanitation and microbiological quality of food and water. The presence of the bacterium *Escherichia coli* the most common fecal indicator, has been used in the past 100 years to monitor incidences of sewage contamination.

Current detection methodologies for *E. coli* or fecal coliforms are based on the properties of acid or gas production from the fermentation of lactose. The most widely used methods are: the Most Probable Number (MPN) assay and the Membrane Filtration (MF)test. Both techniques are approved by the Environmental Protection Agency (EPA) and the American Public Health Association for the microbiological examination of water and waste water.

The MPN method is actually comprised of 3 separate assays. In the Presumptive test, a nonselective medium such as Lauryl Sulfate Tryptose broth (LST) or Lactose broth is used to check for gas production from the fermentation of lactose. Gas positive tubes are then subcultured into a more selective medium, Brillant Green Lactose Bile (BGLB) for coliforms or *E. coli* broth (EC) for fecal coliforms, and again checked for gas production (confirmed test). Samples from positive confirmatory tests are required to be tested further, by plating on a selective and differential medium like Eosin Methylene Blue agar or Endos agar, followed by Gram Stain and biochemical tests to firmly establish the presence of the indicator bacterium (completed test). The entire MPN assay requires up to five days to complete; therefore, it is not cost effective in terms of both time and materials.

The MF techniques for the biological examination of water were introduced in early 1950's. Unlike the MPN assay which was tedious and time consuming, MF analysis could be completed in 24 hours without the need for further confirmations, and the system allowed for the examinations of large volumes of water samples. The basic MP procedure is as follows: a volume of sample, usually 100 ml is filtered through a 0.45 micron pore-diameter filter, and then incubated on a sterile pad saturated with selective medium. The two media most often used are the m-Endo broth, selective for coli-forms at 35° C., and the mFC broth, selective for fecal coliforms at 45° C. Both of these media have been reported to underestimate the actual numbers of bacteria present, due either to the selectivity of the medium or the high temperature used for incubation (45° C.). Such incidences of false negatives have been especially prevalent when the organisms in the sample have been sublethaly injured by environmental factors and/or chemicals.

Recently, modifications have been proposed by the EPA to follow up the MF assay with a confirmatory step using LST broth followed by BGLB broth as in the MPN test. Such modifications even though they would reduce the incidences of false positive and false negative reactions, they would triple the MF assay time from 24 hours to 72 hours.

In 1982, Feng and Hartman (Applied and Environmental Microbiology, Vol. 43 No. 6, June 1982 pp. 1320–1329) introduced a fluorogenic assay for the detection of *E. coli* using the substrate 4-methylumbelliferone glucuronide (MUG). *E. coli* cells produce the enzyme beta-D-glucuronidase which could cleave the substrate, releasing the fluorogenic methyl umbelliferone radical into the Presumptive LST medium. The assay provided both the Presumptive (gas production) and the Confirmed data (fluorescence) for fecal coliforms in a single test within 24 hours. Although the MUG assay was rapid and simple, only 90% of the *E. coli* cells tested produced this enzyme, hence the test was not 100% reliable.

It is evident that currently, no suitable assays exist for the enumeration of coliforms or fecal coliforms. The development of a simple, rapid and reliable detection assay would not only decrease cost and time, but also greatly increase the efficiency of monitoring water sanitation.

The detection system we propose is to use monoclonal antibodies to supplement existing assays. By incorporating the principles of acid and/or gas production from lactose, fluorescence from MUG, along with an Enzyme Linked Immuno-Sorbent Assay (ELISA) using an *E. coli* specific monoclonal antibody all within one test, we can derive several distinct data from a single assay, and provide a fairly reliable detection system for *E. coli*.

SUMMARY OF THE INVENTION

The present invention concerns a method for analyzing a liquid sample to determine the presence of a specific microbe, e.g. *E. coli*.

The method comprises randomly distributing a known volume of the liquid sample onto a suitable membrane material as a defined number of equal volume aliquots. Each of the aliquots is then filtered under appropriate conditions through the membrane material to collect the microbe on the membrane.

The microbe collected on the membrane material from each aliquot is separately contacted with a defined volume of a suitable solution containing a predetermined amount of detectable reagent specific for the microbe e.g. an antibody specific to an antigenic site on the microbe under conditions permitting formation of complexes between the reagent and the microbe.

By determining the amount of complex formed from each aliquot one can determine the amount of microbe originally present in the liquid sample.

In a specific embodiment of the invention additional steps can be added after collecting the microbe on the membrane and before contacting the microbe with the detectable reagent.

These steps comprise contacting the membrane material with a non-selective medium permitting growth of the microbe and incubating the membrane material in contact with the non-selective medium under conditions such that the microbe multiplies a predetermined number of times.

The membrane material in contact with the non-selective medium is then tested for one or more substances indicative of the presence of the microbe. After testing the non-selective medium is removed from contact with the membrane material.

The invention also concerns a device useful for analyzing a liquid sample to quantitatively determine the presence of a specific microbe in the liquid sample.

BRIEF DESCRIPTION OF THE FIGURES

FIG. 1 shows a perspective view of one embodiment of the device showing the plate (1), receptacles (2), upper openings (3), lower openings (4), membrane material (5), reservoir means (6) and support means (7).

FIG. 2 shows a side view of a device having 96 receptacles mounted on a vacuum filtration apparatus (8).

FIG. 3 shows a front view of the device depicted in FIG. 2.

FIG. 4 shows a top view of the device depicted in FIG. 2.

DETAILED DESCRIPTION OF THE INVENTION

The invention concerns a method for analyzing a liquid sample to determine the presence of a specific microbe e.g. E. coli. A known volume of the liquid sample is randomly distributed onto a suitable membrane material as a defined number of equal volume aliquots. Each of the aliquots is filtered under appropriate conditions through the membrane material to collect the microbe on the membrane. The microbe collected on the membrane material from each aliquot is separately contacted with a defined volume of a suitable solution containing a predetermined amount of detectable reagent specific for the microbe e.g. a polynucleotide complementary to one of the microbial genes, or an antibody specific to an antigenic determinant on the microbe, under conditions permitting formation of complexes between the reagent and the microbe. The amount of complex formed from each aliquot is determined e.g. by statistical analysis and thereby the amount of microbe originally present in the liquid sample is also determined.

In a specific embodiment of the invention additional steps are performed after the microbe has been collected on the membrane material and before the microbe is contacted with the detectable reagent. The additional steps comprise contacting the membrane material with a non-selective medium permitting growth of the microbe and incubating the membrane material in contact with the non-selective medium under conditions such that the microbe multiplies a predetermined number of times.

The membrane material in contact with the non-selective medium is tested for one or more substances indicative of the presence of the microbe. After testing the non-selective medium is removed from contact with the membrane material.

The membrane material can be a hydrophobic filter such as a nitrocellulose filter. One of the problems encountered in using such membrane materials is wicking or drawing up of the liquid sample through the membrane. The wicking can be controlled by various methods such as methods which keep the membrane material dry.

One embodiment of the invention concerns a method for analyzing an aqueous sample to determine the presence of a coliform bacterium such as *Escherichia coli*.

The method involves distributing a known volume of the aqueous sample onto a membrane material as a defined number of equal volume aliquots.

A known amount of aqueous sample is then filtered through the membrane material to collect *Escherichia coli* on the membrane material. The membrane material is contacted with a defined volume of a suitable solution containing a predetermined amount of a detectable antibody specific for an antigenic determinant on *Escherichia coli* under conditions permitting formation of a complex between the antibody and *Escherichia coli*. The amount of complex formed is determined and thereby the amount of *Escherichia coli* originally present in the aqueous sample is also determined.

In a variation of this method, additional steps can be performed after the *E. coil* has been collected on the membrane and before it has been contacted with the antibody.

The additional steps comprise contacting the membrane material with a non-selective medium permitting growth of *Escherichia coli*, such as phenol red lactose broth supplemented with 4-methyl-umbelliferone D-glucuronide, and incubating the covered membrane material under conditions such that the *Escherichia coli* multiplies a predetermined number of times.

The covered membrane material is then separately tested for the presence of one or more substances indicative of the presence of *Escherichia coli*. After testing the non-selective medium covering the membrane material is removed.

In a specific embodiment of the invention the antibody used is a monoclonal antibody directed against antigenic sites on the flagellum protein. Antibodies directed to other sites on the microbes surface can also be used. These antibodies may be labeled with detectable markers such as appropriate luminescent compounds or enzymes which are known to those skilled in the art.

The present invention also concerns a device useful for analyzing a liquid sample to quantitatively determine the presence of a specific microbe in the liquid sample.

One embodiment of such a device is illustrated in FIGS. 1–4. The device may be conveniently and inexpensively constructed of a synthetic polymer, e.g. polyacrylate, preferably transparent. The device comprises a plate (1) provided with a number of receptacles (2), the receptacles each defining an upper (3) and lower opening (4). A membrane material (5) e.g. a hydrophobic filter such as a treated nitrocellulose filter, is in communication with the lower opening of each receptacle, the membrane material being pervious so as to permit water which is passed through the upper openings of the receptacle to contact the membrane material and flow out of the lower openings of the receptacles. A reservoir means (6) is located adjacent to the plate for holding the liquid sample and for dispensing the liquid sample through the upper openings of the receptacles. A distribution means is present in the reservoir means for evenly distributing the liquid sample over the plate to randomly distribute microbes in the liquid sample onto the membrane material e.g. by baffler. A support means (7) is located adjacent to, e.g. below, the plate for supporting the device over a vacuum to permit vacuum filtration to draw the liquid sample through the membrane material.

Such a device is useful for analyzing an aqueous sample in accordance with this invention to quantitatively determine the presence of a specific microbe in the sample.

Thus, a known volume of the liquid sample is added to the reservoir means (6) and allowed to be randomly distributed through the upper openings (3) of plate (1) into the receptacles (2) and thence onto the membrane (5) as a defined number of equal volume aliquots. The reservoir means (6) may additionally contain a control means, e.g. a stopcock, for controlling the delivery of the sample from the reservoir means (6) to the receptacles (2). Alternatively, the control means may comprise an endplate, slidably-mounted or rotatably-mounted between the bottom of the reservoir means (6) and the top plate (1). Such an endplate may contain a number of openings which when out of register with the upper openings (3) of plate (1) or openings on an intermediate plate prevent delivery of the sample to the receptacles (2). By filtering each of the aliquots under appropriate conditions through the lower opening (4) of each of the receptacles (2), a microbe present in the sample is collected on the membrane material (5). The amount of such microbe present in the sample is then quantitatively determined in accordance with this invention. For convenience in practicing the methods of this invention, materials such as non-selective growth medium and detectable reagent specific for the microbe, e.g. polynucleotide or antibody, may be separately stored in storage compartments connected to the receptacles (2) by a controlled delivery means, e.g. tubing equipped with a clamp or stopcock connecting the storage compartment(s) to the reservoir means. The storage compartments may be mounted adjacent to plate (1) or at a remote location. In one embodiment one or more storage compartments and the reservoir means (6) are mounted to the top of plate (1) via a controlled delivery means such as a slidably-mounted or rotatably-mounted endplate and support means. Such endplate contains a number of openings which can by sliding or rotating the endplate be brought into register with the upper openings (3) of plate (1) or with openings on a support means above the upper openings (3). By sliding or rotating the endplate the sample in the reservoir means (6) may be delivered to the upper openings (3) on plate (1). After filtration of the sample, material in one or more storage compartments may then be separately delivered to the receptacles (2) by realigning the endplate appropriately. Thus, the controlled delivery means permits the selective delivery of the contents of each storage compartment to the receptacles. In one embodiment the endplate is affixed to the reservoir and storage compartments(s) such that the endplate may be slided or rotated by sliding or rotating the reservoir means (6) and storage compartments. In another embodiment the endplate is mounted to permit sliding or rotating of the endplate independently of the reservoir means (6) and storage compartments. The device of this invention may be manufactured in compact form as a designed cassette which may be attached, e.g. clamped to a vacuum filtration device as depicted in FIGS. 2 and 3. Alternatively, the device may also include a receiving chamber attached to the support means (7) and equipped with a port for connection to a vacuum line.

EXPERIMENTAL SECTION

The present invention concerns a method for determining contaminative microorganisms or chemicals in fluids. As discussed above this method employs a device that will allow for the filtration and compartmentalization of large volumes of fluid to concentrate the contaminant in question. Identification of the contaminant is accomplished by use of specific monoclonal antibodies and/or adjunct tests based on the knowledge of the specific contaminant's functional properties.

Specific application of the invention involves the detection and quantification of coliform and/or *Escherichia coli* in potable water. A specified water sample is filtered through a designed cassette containing a hydrophobic membrane filter with a designated number of separate compartments. Microorganisms present in the water sample are then evenly distributed over a compartmentalized filter.

Since the microorganisms to be quantified are in low numbers in potable water, an enrichment step is employed to raise the number of microorganisms to detectable levels. This is accomplished by overlaying each compartment well of the membrane filter cassette with a small volume of non-selective media (e.g. phenol red lactose broth supplemented with 4-methyl-umbelliferone D-glucuronide). The filter cassette with added medium is then incubated at 35° C. for a designated period of time and then scored for those compartment wells showing an acid reaction based on the pH indicator in the medium. Lactose is the sole carbon source in the medium, therefore acid production will indicate a presumptive positive test for coliform bacteria.

A confirmatory test for the presence of *E. coli* is established by the detection of the fluorogenic radical cleavage product 4-methyl-umbelliferone released by the splitting of the added substrate in the initial enrichment medium by *E. coli*.

Some strains of *E. coli* are lacking the enzyme B-D-glucuronidase, therefore, a completed test based on the employment of specific monoclonal antibodies against one or more common determinants of *E. coli* will be used. To accomplish this final test, the enrichment medium is pulled through the membrane filter leaving the microorganisms retained on the filter. The cassette wells are then overlaid with a small volume of phosphate buffered saline containing one or more *E. coli* specific monoclonal antibodies tagged with an appropriate enzyme or luminescent compound. The antibody-antigen reaction is allowed to occur for a specified time after which unbound antibody is removed from the wells by suction filtration. The antibody "tag" will be developed so that the identification of wells positive for *E. coli* can be determined.

The overall analysis time requires less than 24 hours and provides the investigator with the total number of coliforms and the specific concentration of *E. coli*.

A model study was conducted utilizing both *E. coli* and *Salmonella worthington*. The latter organism was employed since specific antisera were available for this species.

Overnight cultures were grown in LST broth incubated at 37° C. Tenfold serial dilutions were made of each culture so that dilutions were obtained in the range less than or equal to 2 bacteria per ml of liquid sample. Aliquots of these dilutions were spread over petri plates with nutrient agar and incubated overnight at 37° C. to determine the actual number of viable organisms per ml of each dilution used. Concurrently, 0.1 ml of each dilution in the appropriate range was added to the wells of a Millipore "Millititer"™ HA plate (these plates are 96 well microtitration plates backed with a hydrophobic nitrocellulose membrane filter).

The 0.1 ml of fluid containing *E. coli* or *Salmonella worthington* was pulled through the membrane filter by suction filtration thus immobilizing the cells on the filter. Each well was then overlaid with 100 μl of LSTR broth (wells with *E. coli*) or OMEN (wells with *S. worthington*) and incubated for 12 hours at 37° C. After the incubation period, the wells were scored visually for acid production.

Anti-Salmonella flagella antibodies tagged with alkaline phosphatase were added to each well of the cassette after the medium was removed by filtration. The antibody-antigen reaction was allowed to proceed for 30 minutes, after which the unbound antibody was removed by washing each well five times with phosphate-buffered saline. Alkaline phosphatase substrate 1 mg/ml (p-nitrophenol-phosphate, Sigma Chemical Co.) in 10% diethanolamine buffer was added to each well and the reaction scored after 30 minutes. The results are shown below:

Result: *Salmonella worthington*

| Set A | Set B | Set C | Set D | |
|-------|-------|-------|-------|--|
| +++   | +++   | +++   | −+−   | Acid production |
| +++   | +++   | +++   | −+−   | EIA results |

Set A-initially received $1\times10^3$ bacteria
Set B-initially received $1\times10^2$ bacteria
Set C-initially received $1\times10^1$ bacteria
Set D-initially received $1\times10^0$ bacteria There was a 100% correlation with acid production and enzyme immunoassay (EIA) with specific antibody. These tests also indicate that we can recover and specifically identify one organism retained on a filter.

The present invention concerns a rapid *E. coli* detection assay which incorporates several assays into one system. The detection efficiencies of our test system, MUG—Monoclonal Antibody (MUG—MCA) test was compared to the standard MPN with Phenol Red Lactose Broth (PRLB), and MF with mEndo broth, using artificially contaminated water samples.

*E. coli* strain #51, obtained from H. Ochman and R. K. Selander, University of Rochester, Rochester, N.Y., was used for this study. The organism is a MUG (+) strain, and isolated from a human infant. All media used were commercial products obtained from Difco Laboratories (Detroit, Mich.), and prepared as per specifications. The fluorogenic substrate 4-methylumbelliferone glucuronide (MUG) was obtained from Hach Chemical Co. (Ames, Iowa).

Two microliters of an overnight culture of *E. coli* strain #51 grown in Brain Heart Infusion (BHI) broth was used to inoculate 500 mls. of sterile tap water. From the seeded flask, one-tenth dilutions were made in 4.5 ml. Phosphate Buffered Saline blanks (PBS; NaCl, 8.5 g; $Na_2HPO_4$, 1.02 g; $NaH_2PO_4.H_2O$, 0.386 g; distilled $H_2O$, 1000 ml, pH 7.2) and diluted to extinction. 0.1 ml aliquots of appropriate dilutions were used to inoculate into: 1) Nutrient Agar (NA) plates for standard plate count; 2) PRLB-MUG tubes for a 5-tube MPN assay; and 3) 100 ml sterile tap water blanks for the MF and our MUG-MCA test.

In the MF assay, 100 ml of seeded water sample was filtered through a Gelman Metricelmembrane with a 0.45 micron pore diameter. The filter was aseptically transferred onto a sterile pad saturated with mEndo medium, and incubated at 35° C. *E. coli* cells produce green sheen colonies on mEndo medium.

For our MUG—MCA assay, 100 ml of seeded tap water was aseptically filtered through a Millipore Millititer HA plate equipped with a 0.45 micron pore diameter nitrocellulose filter bottom. After filtration, the plate bottom was briefly dried at 35° C. and overlayed with 0.2 ml of PRLB-MUG medium per well.

All tests were set up in duplicate, and incubated at 35° C. overnight (approximately 16 hours).

The following day, the numbers of colonies on NA plates and the sheen colonies on mEndo filter pads were counted and recorded. The PRLB-MUG tubes were examined for positive acid production (pH indicator change from red to yellow) and gas production (gas trapped in Durham vials), and fluorescence from the cleavage of MUG. MPN combinations of positive reactions were then determined for each category for enumeration from a MPN table. On the MUG—MCA test, the 96-well plate was examined, and the number of acid positive (yellow) and fluorescent postive wells were counted and recorded.

To proceed with the confirmatory Enzyme Linked Immunosorbent Assay (ELISA) using a specific monoclonal antibody, spent media in the 96-well plate was filtered through, trapping the bacteria on the membrane. Each well was filtration-washed with 0.1 ml of 3% Bovine Serum Albumin (BSA, Sigma Chemical Co., St. Louis, Mo.) solution in PBS, then incubated with 0.25 ml of the same solution for 1 hour at 35° C. to block non-specific binding by the antibody or conjugate. To remove the BSA solution, the plate was again filtered, and 50 microliters of 30G4 mouse cell line supernatant (mono-clonal antibody) was added per well. This particular monoclonal antibody was induced in mice using purified *E. coli* flagellin protein. The plate was incubated at 35° C. for 1 hour to allow the antibody to bind to its specific antigen (*E. coli* cells), and subsequently, any unbound antibody was removed from the wells by two filtration—washes with PBS.

An affinity purified alkaline phosphatase labelled goat antibody to mouse IgA, IgG, IgM (H+L) (conjugate, KPL, Gaithersburg, Md.) was diluted 1:1000 in PBS and 50 microliter aliquots were added to each well. Conjugate incubation at 35° C. for one hour allowed the conjugated goat anti-mouse antibody to bind to the already antigen-bound mouse monoclonal antibody. Any unbound conjugate was removed by four filtration—washes with PBS containing 0.05% (volume/volume) Tween 20 (Baker Chemical Co., Phillipsberg, N.J.). The substrate used for the phosphate conjugate was sodium para-nitrophenyl phosphate (Sigma Chemical Co., St. Louis, Mo.), prepared at a final concentration of 1 mg/ml in 10% diethanolamine buffer (Diethanolamine, 97 ml.; $NaN_3$ 0.2 g.; $MgCl.6H_2O$, 100 mg.; and distilled water, 800 ml., pH 9.8). The substrate was added in 200 microliter aliquots per well, and the plate incubated at 35° C. for 30 minutes. Reactions in the wells were monitored instrumentally with a Titertek Multiskan (Flow Laboratories), to determine the number of positive wells.

The detection efficiencies of each method described was compared in relation to the number of colonies obtained by Standard Plate Count on NA plates.

Results

The results of a single assay are presented as an example of how the data was recorded, analyzed and compared. The composite results from 3 separate assays will then be presented.

TABLE 1

| Method | Dilution | | | Count |
|--------|----------|--|--|-------|
| | $10^{-2}$ | | | |
| SPC - NA | plate 1 - 140 | | | $1.41 \times 10^4$ cells/ml |
| | plate 2 - 142 | | | |
| | $10^{-3}$ | $10^{-4}$ | $10^{-5}$ | |
| MPN-PRLB-MUG | | | | |
| acid production | 5+* | 3+ | 2+ | $1.4 \times 10^4$ cells/ml** |
| gas production | 5+ | 3+ | 2+ | |
| MU production | 5+ | 3+ | 2+ | |
| MF | $10^{-3}$ | | | |
| filter 1 | 10 | | | $1.1 \times 10^4$ cells/ml |
| filter 2 | 12 | | | |
| MUG-MCA | $10^{-3}$ | | | |
| | Poisson | | | |

TABLE 1-continued

| Method | | Dilution | Count | |
|---|---|---|---|---|
| | | Analysis | | |
| acid (+) | plate 1 | 13 | 14 | |
| | plate 2 | 9 | 9.5 | $1.175 \times 10^4$ cells/ml |
| MUG (+) | plate 1 | 13 | 14 | |
| | plate 2 | 9 | 9.5 | $1.175 \times 10^4$ cells/ml |
| MCA (+) | plate 1 | 13 | 14 | |
| | plate 2 | 12 | 12.7 | $1.33 \times 10^4$ cells/ml |

*number of positive tubes
**(lower limit = $3.7 \times 10^3$)
(upper limit = $3.4 \times 10^4$)

TABLE 2

Test: Millititer HA, *E. coli*

| Row/Col 1 | Col 2 | Col 3 | Col 4 | Col 5 | Col 6 | Col 7 | Col 8 | Col 9 | Col 10 | Col 11 | Col 12 |
|---|---|---|---|---|---|---|---|---|---|---|---|
| | | | | | Plate number: 1 | | | | | | |
| A | 0.099 | 0.127 | 0.076 | 0.100 | 0.100 | 0.148 | 0.091 | 1.103* | 0.128 | 0.134 | 0.115 | 0.092 |
| B | 0.161 | 0.144 | 0.114 | 0.146 | 1.225* | 0.214 | 1.031* | 0.135 | 0.167 | 1.393* | 0.156 | 0.149 |
| C | 1.286* | 0.105 | 0.139 | 0.137 | 0.126 | 0.963* | 0.860* | 0.160 | 0.154 | 1.099* | 0.163 | 0.141 |
| D | 0.117 | 0.120 | 0.136 | 0.144 | 0.143 | 0.190 | 0.153 | 0.215 | 0.157 | 0.164 | 0.182 | 0.133 |
| E | 0.145 | 0.158 | 0.111 | 0.156 | 0.137 | 0.182 | 0.143 | 0.174 | 0.210 | 0.183 | 1.249* | 0.189 |
| F | 1.169* | 0.175 | 0.123 | 0.160 | 0.145 | 0.190 | 0.151 | 1.188* | 0.185 | 0.172 | 0.167 | 0.145 |
| G | 0.159 | 0.174 | 0.151 | 0.148 | 1.240* | 0.120 | 0.163 | 0.214 | 1.191* | 0.174 | 0.184 | 0.153 |
| H | 0.184 | 0.178 | 0.170 | 0.175 | 0.099 | 0.171 | 0.192 | 0.147 | 0.187 | 0.227 | 0.216 | 0.177 |
| | | | | | Plate number: 2 | | | | | | |
| A | 0.154 | 1.351* | 0.172 | 0.159 | 0.181 | 0.116 | 0.138 | 0.119 | 0.095 | 0.192 | 0.124 | 0.158 |
| B | 0.195 | 0.148 | 0.163 | 0.189 | 0.189 | 0.152 | 0.147 | 0.160 | 0.209 | 0.183 | 0.162 | 0.164 |
| C | 0.186 | 0.184 | 0.173 | 0.280 | 1.180+ | 0.938* | 0.193 | 0.171 | 0.134 | 1.012* | 0.159 | 0.115* |
| D | 0.199 | 0.228 | 0.178 | 0.242 | 0.220 | 0.180 | 1.262* | 0.195 | 0.132 | 0.198 | 0.175 | 1.514* |
| E | 0.234 | 0.170 | 0.172 | 0.194 | 0.238 | 0.976+ | 0.148 | 0.207 | 0.195 | 0.245 | 0.242 | 0.212 |
| F | 1.567* | 0.190 | 1.592* | 0.177 | 0.242 | 0.219 | 0.219 | 0.164 | 0.140 | 0.180 | 0.153 | 0.175 |
| G | 0.306 | 0.250 | 0.188 | 0.768* | 0.259 | 0.200 | 0.169 | 0.137 | 0.197 | 0.194 | 0.230 | 0.216 |
| H | 0.272 | 0.252 | 0.270 | 0.215 | 0.207 | 0.184 | 0.236 | 0.202 | 1.350* | 0.240 | 0.234 | 0.295 |

Data for the ELISA using 30G4 MCA is shown in Table 2.
Wells with an asterisk were positive for acid, fluorescence, and ELISA.
The two wells marked with (+) in plate 2 were negative or weakly positive for acid and fluorescence.

Using the counts obtained on SPC as the absolute value of 100% detection, the following detection efficiencies were obtained for the other assays.

TABLE 3

| SPC | - $1.41 \times 10^4$ cells/ml - | 100% |
|---|---|---|
| MPN | - $1.4 \times 10^4$ cells/ml - | 99% |
| MF | - $1.1 \times 10^4$ cells/ml - | 78% |
| | | Poisson Analysis |
| MUG-MCA acid/MUG | - $1.1 \times 10^4$ cells/ml | 83% |
| MCA | - $1.2 \times 10^4$ cells/ml | 90% |

Table 1 shows that in the MPN-PRLB-MUG tube assay, 100% correlation was obtained between acid production, gas production, and fluorescence as expected. The effectiveness of incorporating MUG in conventional water analysis media has been previously documented by Feng and Hartman (Applied and Environmental Microbiology Vol. 43 No. 6 June 1982 pp. 1320–1329). Based on the combination of positive tubes (5 3 2), a bacterial count of $1.4 \times 10^4$ cells/ml was derived from the MPN Table. Since MPN is a statistical assay based on probabilities, the data is provided with 95% confidence limits. In this case, the lower limit was $3.7 \times 10^3$ and the upper limit $3.4 \times 10^4$. The confidence limit simply suggests with 95% certainty that the actual number of bacteria present in the sample lies between the given lower and upper limits. The count estimated by the MPN assay was indeed very close (99%) to the absolute value obtained by SPC (Table 3).

The MF assay detected $1.1 \times 10^4$ cells/ml, or 78% of the actual number of cells present (Table 3). The selectivity and inhibitory effects of mEndo medium is well documented and may have accounted for the slightly lower detection level observed with this assay.

In the conventional portion of our MUG-MCA test, good correlation was again observed between acid production from lactose, and fluorescence. Every well positive for acid was also positive for fluorescence. Assuming that each positive well received 1 cell/well, which is likely, due to the high dilution of the inoculum used; then, the number of positive wells should reflect the number of colonies or bacteria present initially. The count of $1.1 \times 10^4$ cells/ml obtained based on acid and fluorescence was slightly lower than that obtained by SPC (78%); however, it was very compatible with the results of the MF assay. It is possible, that due to random distribution, some of the wells received more than 1 cell/well, thereby, reducing the number of positive wells on the plate.

Table 3 shows that the ELISA portion of the assay using a specific MCA appears to be more sensitive than the conventional (acid-MUG) part of the test. This may be explained by the fact that two wells marked (+) on plate 2 were negative or weakly positive by acid and fluorescence, but were definitely positive by ELISA (Table 2). Perhaps the cells in these wells had not reached maximum beta galactosidase (acid production) and beta-glucuronidase (fluorescence) enzyme production levels, but were present in sufficient numbers to be detected by ELISA.

To summarize the results of the above experiment, it appears that our MUG-MCA assay is compatible to existing EPA approved methods in the analysis of water samples. The detection efficiency attained with the conventional portion (acid-fluorescence) of the test was equal to that obtained with the MF technique. By supplementing the acid-MUG assay with an ELISA using a specific MCA, an even greater efficiency of 85% was attained.

In order to confirm the above findings, three similar experiments were conducted, and the composite data are presented in Table 4.

TABLE 4

| | Assays | | Individual Detection Percentages | Overall Detection Percentage |
|---|---|---|---|---|
| SPC-NA plates | 1) | $1.4 \times 10^4$ | 100 | 100% |
| | 2) | $4.2 \times 10^3$ | 100 | |
| | 3) | $1.1 \times 10^4$ | 100 | |
| MPN | 1) | $1.4 \times 10^4$ | 100 | 65% |
| | 2) | $2.7 \times 10^3$ | 64 | |
| | 3) | $3.5 \times 10^3$ | 32 | |
| MF | 1) | $1.1 \times 10^4$ | 78 | 93% |
| | 2) | $5.0 \times 10^3$ | 119 | |
| | 3) | $9.5 \times 10^3$ | 83 | |
| acid/MUG | 1) | $1.175 \times 10^4$ | 84 | 69% |
| | 2) | $2.55 \times 10^3$ | 59.5 | |
| | 3) | $7.2 \times 10^3$ | 63.6 | |
| MCA | 1) | $1.28 \times 10^4$ | 91 | 89% |
| | 2) | $4.10 \times 10^3$ | 95 | |
| | 3) | $8.9 \times 10^3$ | 81 | |

The average counts of 3 assays and the overall detection percentages are listed for each method (Table 4). The 69% detection efficiency obtained for MPN was abnormally low in comparison to SPC, and attributed mostly to the results of assay #3. In that example, although the SPC obtained ($1.1 \times 10^4$ cells/ml) was within the acceptable upper bound of the 95% confidence limit ($1.1 \times 10^4$ cells/ml) the count of $3.5 \times 10^3$ cells/ml estimated by MPN amounted to only a 32% detection efficiency. Statistical analysis based on probability such as MPN has been reported to overestimate as well as underestimate the actual values; hence, the results of assay #3 were not unusual.

The 93% overall detection efficiency recorded for MF was better than expected. The mEndos medium used for this test has been known to be inhibitory, especially to chemical or environmentally stressed cells. It is possible that the detection efficiency by MF in actual water analysis situations may be significantly lower than that recorded here.

Comparisons of MUG-MCA assay with the EPA approved methods showed that the conventional (acid-MUG) portion of our test is compatible, and slightly better than the MPN assay (Table 4). Moreover, by incorporating the ELISA portion using a specific MCA, the detection efficiency was raised to 89%, approaching that obtained by MF. The presence of negative/weakly positive acid and fluorescent wells accounted for the difference in detection efficiency between the conventional (acid-MUG) portion and the ELISA (MCA) portion of our test. In the 3 assay replicates, a total of 8 wells were encountered, which were negative/weakly positive for acid and fluorescence, but were definitely positive by ELISA. Such high incidences of weak acid-fluorescent wells may be explained by the findings of Feng and Hartman, who reported that a minimum of 16 hour incubation was required before a single *E. coli* cell can multiply to levels that will produce detectable fluorescence. Since a 16 hour incubation period was used in our MUG-MCA test, it is possible that the cells in some of the wells had not yet produced sufficient enzymes to provide detectable acidity and fluorescence.

In summary, our MUG-MCA assay proved to be as equally efficient as the EPA approved methods for the analysis of *E. coli* in water samples. Unlike the MPN and the MF techniques which are time consuming and require further confirmatory reactions (not done in the example), our assay can provide presumptive (acid production), confirmed (fluorescence), and completed (MCA-ELISA) reactions for *E. coli* all in one plate and within 24 hours.

What is claimed is:

1. A method for analyzing a liquid sample to quantitatively determine the presence of a specific microbe which comprises:

distributing a defined volume of a liquid sample as a number of equal volume aliquots into a number of receptacles each associated with membrane material so that the microbe is randomly distributed on the membrane material associated with said receptacles, filtering the aliquots to collect on the membrane material microbes contained in the liquid sample and sequentially performing in a single assay 1. a first test to determine the presumptive presence of the specific microbe and to confirm the presence of the microbe, which first test comprises:

(a) contacting the membrane material with a selective medium permitting growth of the microbes collected, said medium including metabolizable substrates;

(b) incubating the membrane material so that the microbes multiply;

(c) analyzing the medium for a metabolic by-product which indicates the presumptive presence of the specific microbe to be determined and for the presence of another metabolic by-product which confirms the presence of said microbe; and (d) removing the non-selective medium from the membrane material and 2. a second test to completely determine and quantify the presence of the microbe, which second test comprises:

(a) contacting the microbe collected on the membrane material with a predetermined amount of a detectable reagent specific for the microbe to be determined under conditions permitting formation of complexes between the reagent and the microbe and (b) determining the amount of complex formed and thereby the amount of the specific microbe originally present in the liquid sample.

2. A method for analyzing an aqueous sample to quantitatively determine the presence of a specific microbe which comprises:

distributing a defined volume of an aqueous sample as a number of equal volume aliquots into a number of receptacles each associated with a membrane material so that the microbe is randomly distributed on the membrane material associated with said receptacles, filtering the aliquots to collect on the membrane material microbes contained in the aqueous sample, performing in a single assay 1. a first test to determine the presumptive presence of the specific microbe and to confirm said presence of the microbe, which first test comprises:

(a) contacting the membrane material with a non-selective medium permitting growth of the microbes collected said medium including metabolizable substrates;

(b) incubating the membrane material so that the microbes multiply;

(c) analyzing the medium for the presence of a metabolic by-product which indicates the presumptive presence of the microbe and for the presence of another metabolic by-product which confirms the presence of the microbe; and (d) removing the non-selective medium from the membrane material and 2. a second test to completely determine and quantify the presence of the microbe, which second test comprises:

(a) contacting the microbe collected on the membrane material with a predetermined amount of a detectable reagent specific for the microbe to be determined under conditions permitting formation of complexes between the reagent and the microbe; and (b) determining the amount of complex formed and thereby the amount of the specific microbe originally present in the liquid sample.

3. The method of claim 1 wherein the reagent is a polynucleotide complementary to a gene of the microbe.

4. The method of claim 1 wherein the specific microbe is a coliform bacterium.

5. The method of claim 1 wherein the reagent is an antibody specific for an antigenic determinant of the microbe.

6. The method of claim 1 wherein the reagent is a monoclonal antibody specific for the microbe.

7. The method of claim 1 wherein the membrane material is a hydrophobic filter.

8. The method of claim 1 wherein the determination of the amount of microbe originally present in the liquid sample is by means of statistical analysis.

9. The method of claim 2 wherein the membrane material is a hydrophobic filter.

10. The method of claim 2 wherein the specific microbe is *Escherichia coli* and wherein the detectable antibody of the second test is specific for an antigenic determinant on *Escherichia coli*.

11. The method of claim 10 wherein the determination of the amount of *Escherichia coli* originally present in the aqueous sample is by means of statistical analysis.

12. The method of claim 10 wherein the detectable antibody is a monoclonal antibody specific for *Escherichia coli*.

13. The method of claim 10 wherein the detectable antibody in an *Escherichia coli* specific monoclonal antibody tagged with an appropriate luminescent compound.

14. The method of claim 12 wherein the *Escherichia coli* specific monoclonal antibody is directed against antigenic sites on the flagellum protein.

15. The method of claim 10 wherein the non-selective medium is phenol red lactose broth and a metabolizable substrate is 4-methyl-umbelliferone-D-glucuronide.

16. The method of claim 15 wherein the metabolic by-product which indicates the presumptive presence of the *Escherichia coli* is carbon dioxide and wherein the other metabolic by-product which confirms the presence of the *Escherichia coli* is 4-methyl-umbelliferone.

17. A method for analyzing a liquid sample to quantitatively determine the presence of a viable specific microbe which comprises distributing a defined volume of a liquid sample as a number of equal volume aliquots into a number of receptacles each associated with membrane material so that the microbe is randomly distributed on the membrane material associated with said receptacles, filtering the aliquotes to collect on the membrane material microbes contained in the liquid sample and sequentially performing in a single assay a first test to determine the presumptive presence of the specific microbe and to confirm the presence of the microbe, which first test comprises:

(a) contacting the membrane material with a non-selective medium permitting growth of the microbes collected, said medium including metabolizable substrates;

(b) incubating the membrane material so that the microbes multiply;

(c) analyzing the medium for a metabolic by-product which indicates the presumptive presence of the viable specific microbe to be determined and for the presence of another metabolic by-product which confirms the presence of said viable microbe; and (d) removing the non-selective medium from the membrane material and a second test to completely determine and quantify the presence of the microbe, which second test comprises:

(a) contacting the microbe collected on the membrane material with a predetermined amount of a detectable immunoreactive reagent specific for the microbe to be determined under conditions permitting formation of complexes between the immunoreactive reagent and the microbe, (b) completing the identification of the microbe based on said complex and (c) determining the amount of complex formed and thereby the amount of the specific microbe originally present in the liquid sample.

18. An assay method for analyzing a liquid sample to quantitatively determine the presence of a specific microbe which comprises distributing a defined volume of a liquid sample as a number of equal volume aliquots into a number of receptacles, each receptacle being associated with membrane material, so that microbe is randomly distributed on the membrane material associated with said receptacles, filtering the aliquots to collect on the membrane material microbes contained in the liquid sample and sequentially performing in a single assay a first test to determine the presumptive presence of the specific microbe and to confirm the presence of the microbe, which first test comprises:

(a) contacting the membrane material with a non-selective medium permitting growth of the microbes collected, said medium including metabolizable substrates;

(b) incubating the membrane material so that the microbes multiply;

(c) analyzing the medium (i) for a metabolic by-product which indicates the presumptive presence of the specific microbe to be determined and (ii) for the presence of another metabolic by-product which confirms the presence of said microbe and (d) removing the non-selective medium from the membrane material and a second test to completely determine and quantify the presence of the microbe, which second test comprises:

(a) contacting the microbe collected on the membrane material with a predetermined amount of a detectable reagent specific for the microbe to be determined, which reagent comprises a polynucleotide complementary to a gene material of the microbe, under conditions permitting formation of complexes between the reagent and the microbe and (b) determining the amount of complex formed and thereby the amount of the specific microbe originally present in the liquid sample.

19. An assay method for analyzing a liquid sample to quantitatively determine the presence of a coliform-type microbe which comprises distributing a defined volume of a liquid sample as a number of equal volume aliquots into a number of receptacles, each receptacle being associated with membrane material, so that the microbe is randomly distributed on the membrane material associated with said receptacles, filtering the aliquots to collect on the membrane material microbes contained in the liquid sample and sequentially performing in a single assay a first test to determine the presumptive presence of the specific microbe and to confirm the presence of the microbe, which first test comprises:

(a) contacting the membrane material with a non-selective medium permitting growth of the microbes collected, said medium including metabolizable substrates;

(b) incubating the membrane material so that the microbes multiply;

(c) analyzing the medium (i) for a metabolic by-product which indicates the presumptive presence of the specific microbe to be determine and (ii) for the presence of another metabolic by-product which confirms the presence of said microbe and (d) removing the non-selective medium from the membrane material and a second test to completely determine and quantify the presence of the microbe, which second test comprises:

(a) contacting the microbe collected on the membrane material with a predetermined amount of a detectable reagent specific for the microbe to be determined, which reagent comprises an antibody specific for an antigenic determinant of the microbe, under conditions permitting formation of complexes between the reagent and the microbe and (b) determining the amount of complex formed and thereby the amount of the specific microbe originally present in the liquid sample.

20. An assay method for analyzing a liquid sample to quantitatively determine the presence of a viable *Escherichia coli* microbe which comprises distributing a defined volume of a liquid sample as a number of equal volume aliquots into a number of receptacles, each receptacle being associated with membrane material, so that the microbe is randomly distributed on the membrane material associated with said receptacles, filtering the aliquots to collect on the membrane material microbes contained in the liquid sample and sequentially performing in a single assay a first test to determine the presumptive presence of the specific microbe and to confirm the presence of the microbe, which first test comprises:

(a) contacting the membrane material with a non-selective medium permitting growth of the microbes collected, said medium including metabolizable substrates;

(b) incubating the membrane material so that the microbes multiply;

(c) analyzing the medium for a metabolic by-product which indicates the presumptive presence of the specific microbe to be determine and for the presence of another metabolic by-product which confirms the presence of said microbe; and (d) removing the non-selective medium from the membrane material and a second test to completely determine and quantify the presence of the microbe, which second test comprises:

(a) contacting the microbe collected on the membrane material with a predetermined amount of a detectable reagent specific for the microbe to be determined, said reagent comprising an antibody directed against antigenic sites on the flagellum protein of *Escherichia coli* under conditions permitting formation of complexes between the reagent and the microbe and (b) determining the amount of complex formed and thereby the amount of the specific microbe originally present in the liquid sample.

21. A method for the detection and quantification of a specific viable microbe present in a liquid sample, and particularly adapted for the detection and quantification of low concentrations of said specific viable microbes, comprising a. randomly distributing any such microbes into a plurality of specimens by distributing a defined volume of a liquid sample as a number of substantially equal volume aliquots into a corresponding number of receptacles so that any such microbes are randomly distributed among the receptacles, each receptacle having a porous membrane, material associated with it;

b. filtering the aliquots through the respective porous membrane material associated with each receptacle and collecting any such microbes on the membrane material;

c. enriching any such microbes to raise the number of any such viable microbes by i. contacting the membrane material, and any such microbes, with a nonselective medium permitting growth of the specific microbe, said medium including substrates metabolized by said microbe;

ii. incubating the membrane material, and any such microbes, to permit any such microbes to multiply a predetermined number of times, d. in a single assay sequentially i. performing a first test comprising a) analyzing the medium for a first by-product of the metabolism of viable specific microbes, said first by-product being indicative of the presumptive presence of viable specific microbes, and b) a second byproduct of the metabolism of viable specific microbes, said second byproduct being confirmatory of the presence of viable microbes, ii. removing the nonselective medium from the membrane material and iii. based on the results of the first test identifying specimens that have viable microbes, selectively performing a second test on those specimens evidencing viable specific microbes, said second test comprising a) contacting said viable microbes collected on the membrane material with a predetermined amount of a detectable reagent that is immunoreactive with respect to the specific microbe,
b) reacting the microbe and reagent under conditions permitting complex formation between the reagent and the specific microbe,
c) completing the identification of the specific microbe based on thus-formed complexes, and
d) determining the amount of thus-formed complexes and
iv. determining the amount of viable specific microbes present in the original liquid sample based on the amount of thus-formed complexes and the predetermined number of multiplications in step c.ii.

* * * * *